United States Patent
Koehler

(10) Patent No.: US 8,660,313 B2
(45) Date of Patent: Feb. 25, 2014

(54) CORRECTION FOR UN-VOLUNTARY RESPIRATORY MOTION IN CARDIAC CT

(75) Inventor: Thomas Koehler, Norderstedt (DE)

(73) Assignee: Koninklijke Philips N.V., Eindhoven (NL)

(*) Notice: Subject to any disclaimer, the term of this patent is extended or adjusted under 35 U.S.C. 154(b) by 279 days.

(21) Appl. No.: 12/746,301

(22) PCT Filed: Dec. 12, 2008

(86) PCT No.: PCT/IB2008/055257
§ 371 (c)(1), (2), (4) Date: Jun. 4, 2010

(87) PCT Pub. No.: WO2009/081316
PCT Pub. Date: Jul. 2, 2009

(65) Prior Publication Data
US 2010/0272322 A1 Oct. 28, 2010

Related U.S. Application Data

(60) Provisional application No. 61/014,885, filed on Dec. 19, 2007.

(51) Int. Cl.
*G06K 9/00* (2006.01)

(52) U.S. Cl.
USPC ........... 382/107; 382/128; 382/130; 382/131; 382/132

(58) Field of Classification Search
USPC ................ 382/107, 128, 130–132, 236
See application file for complete search history.

(56) References Cited

U.S. PATENT DOCUMENTS

| | | | |
|---|---|---|---|
| 4,994,965 A | 2/1991 | Crawford et al. | |
| 5,271,055 A | 12/1993 | Hsieh et al. | |
| 6,426,990 B1 * | 7/2002 | Cesmeli | 378/8 |
| 6,501,979 B1 * | 12/2002 | Manning et al. | 600/413 |
| 6,865,248 B1 * | 3/2005 | Rasche et al. | 378/8 |
| 8,184,883 B2 | 5/2012 | Grass et al. | |
| 2005/0096538 A1 * | 5/2005 | Chomas et al. | 600/437 |
| 2005/0203373 A1 * | 9/2005 | Boese et al. | 600/407 |
| 2006/0140335 A1 * | 6/2006 | Heuscher et al. | 378/4 |

(Continued)

FOREIGN PATENT DOCUMENTS

| | | | | |
|---|---|---|---|---|
| EP | 1394747 A1 | 3/2004 | | |
| WO | WO 2005063125 A1 * | 7/2005 | | A61B 8/08 |

(Continued)

OTHER PUBLICATIONS

Schafer, D., Motion-Compensated and Gated Cone Beam Filtered Back-Projection for 3-D Rotational X-Ray Angiography; 2006; IEEE Trans on Medical Imaging; 25(7)898-906.

*Primary Examiner* — Matthew Bella
*Assistant Examiner* — Weiwen Yang

(57) ABSTRACT

A CT angiography apparatus compensates for respiratory motion. During a helical scan, a radiation source and a detector generate data sets corresponding to a plurality of sub-volumes of a blood vessel over a plurality of cardiac cycles. Sub-volume data sets corresponding to a selected cardiac phase are reconstructed into a plurality of sub-volume images. Characteristic points in the sub-volume images are identified. A computer routine or processor calculates a respiratory motion vector based on the identified characteristic points in a plurality of the sub-volume images. An image reconstruction routine or processor reconstructs the original sub-volume data in the selected cardiac phase into a volume image representation using the calculated respiratory motion vector.

16 Claims, 3 Drawing Sheets

(56) References Cited

U.S. PATENT DOCUMENTS

2006/0235295 A1 10/2006 Boese et al.
2006/0285632 A1 12/2006 Boese et al.
2007/0116172 A1 5/2007 Hsieh et al.
2007/0153971 A1 7/2007 Wang et al.

FOREIGN PATENT DOCUMENTS

| | | |
|---|---|---|
| WO | 2005099382 A2 | 10/2005 |
| WO | 2007015199 A2 | 2/2007 |
| WO | 2007060572 A2 | 5/2007 |
| WO | 2007072286 A2 | 6/2007 |

* cited by examiner

CORRECTION FOR UN-VOLUNTARY RESPIRATORY MOTION IN CARDIAC CT

CROSS REFERENCE TO RELATED APPLICATIONS

This application claims the benefit of U.S. provisional application Ser. No. 61/014,885 filed Dec. 19, 2007, which is incorporated herein by reference.

The present application relates to computerized tomographic (CT) imaging. It finds particular application in conjunction with coronary artery angiography and will be described with particular reference thereto. However, these concepts will also find application in conjunction with other CT applications in the thorax and abdomen.

In CT coronary artery angiography, a patient is commonly injected with a contrast agent. When the contrast agent reaches the coronary artery to be imaged, a CT scanner starts collecting image data. The patient holds his/her breath and the CT data is collected, such that all data is collected in a common respiratory phase. During the data collection period, a high speed helical CT scan is conducted with a relatively low pitch. The data is retrospectively gated to generate a data set in a selected cardiac phase. The low pitch generates a sufficient amount of redundant data such that when the data outside of the selected cardiac phase can be discarded, a complete data set in the selected cardiac phase remains.

This technique works well if the patient can hold their breath during the 5-20 second data acquisition period. If the patient does not or cannot hold their breath for the entire data acquisition time, then the coronary artery angiography technique must be repeated. However, due to dose limits on the contrast agents, the process must be repeated at a later time. Typically, the data cannot be retrospectively gated for both cardiac and respiratory motion and still produce a complete set of data in the selected cardiac and respiratory phases for reconstruction. Rather, because the respiratory cycle is relatively slow compared to the cardiac cycle, significant sections of data along the coronary artery would be lost if cardiac and respiratory gating were both applied to this data.

The present application describes a technique for correcting for respiratory motion during cardiac CT image data acquisition.

In accordance with one aspect of the present application, a method of CT angiography with respiratory motion compensation is provided. A computer readable medium on which a program is stored controls a processor to implement the steps. Data sets corresponding to a plurality of sub-volumes of a blood vessel are generated over a plurality of cardiac cycles. Sub-volume images are generated from the sub-volume data sets. Characteristic points in the sub-volume images are identified. A respiratory motion vector is calculated for at least some of the sub-volumes based on the identified characteristic points. The sub-volume data sets are reconstructed into a volume representation in accordance with the calculated respiratory motion vector.

In accordance with another aspect, a CT angiography apparatus with respiratory motion compensation is provided. The radiation source and detector generate data sets corresponding to a plurality of sub-volumes of a blood vessel over a plurality of cardiac cycles. A sub-volume reconstruction routine or processor generates sub-volume images from the sub-volume data sets. A characteristic point routine or processor identifies characteristic points in the sub-volume images. A respiratory motion routine or processor calculates a respiratory motion vector for at least some of the sub-volumes based on the identified characteristic points. An image reconstruction routine or processor reconstructs the sub-volume data into an image representation in accordance with the calculated respiratory motion vector.

In accordance with another aspect, a CT angiography apparatus includes a means for generating data sets corresponding to a plurality of sub-volumes of an anatomical region of a plurality of cardiac cycles. A means generates sub-volume images from the sub-volume data sets. A means identifies characteristic points in the sub-volume images. A means calculates a respiratory motion vector for at least some of the sub-volume images based on the characteristic points. A means reconstructs the sub-volume data into a volume image representation in accordance with the calculated respiratory motion vector.

One advantage is it enables cardiac CT angiography to be performed on people who cannot or will not hold their breath during the data acquisition, e.g. pediatric patients, patients with respiratory disease, unconscious patients, and the like.

Another advantage resides in minimizing contrast agent dosages.

Another advantage resides in respiratory motion corrected CT angiography images.

Still further advantages will become apparent to those of ordinary skill in the art upon reading and understanding the following detailed description.

The drawings are only for illustrative purposes and are not to be construed as limiting the invention.

Figure 1:
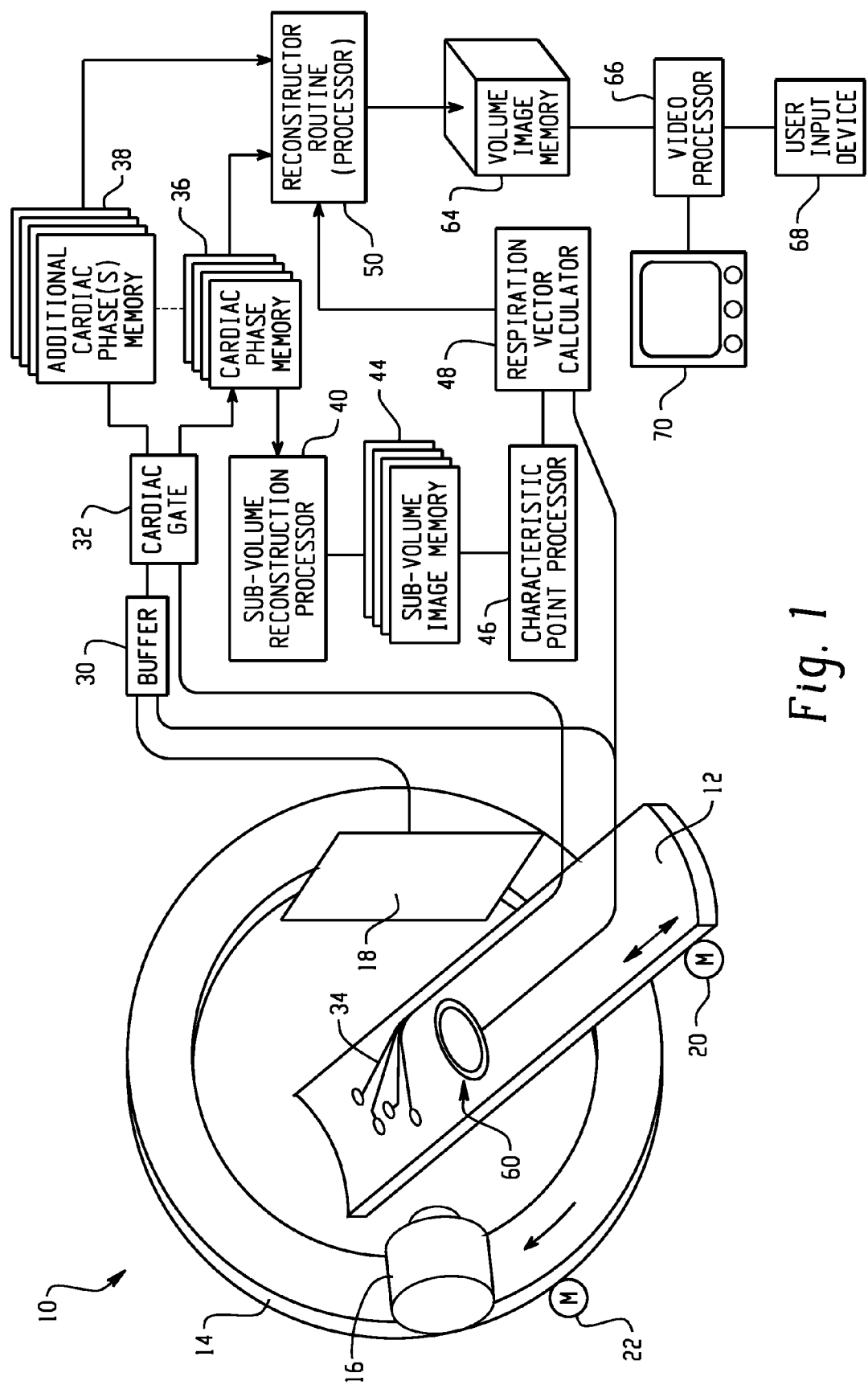
FIG. 1 is a diagrammatic illustration of a CT scanner system in accordance with the present application.
Figure 2:
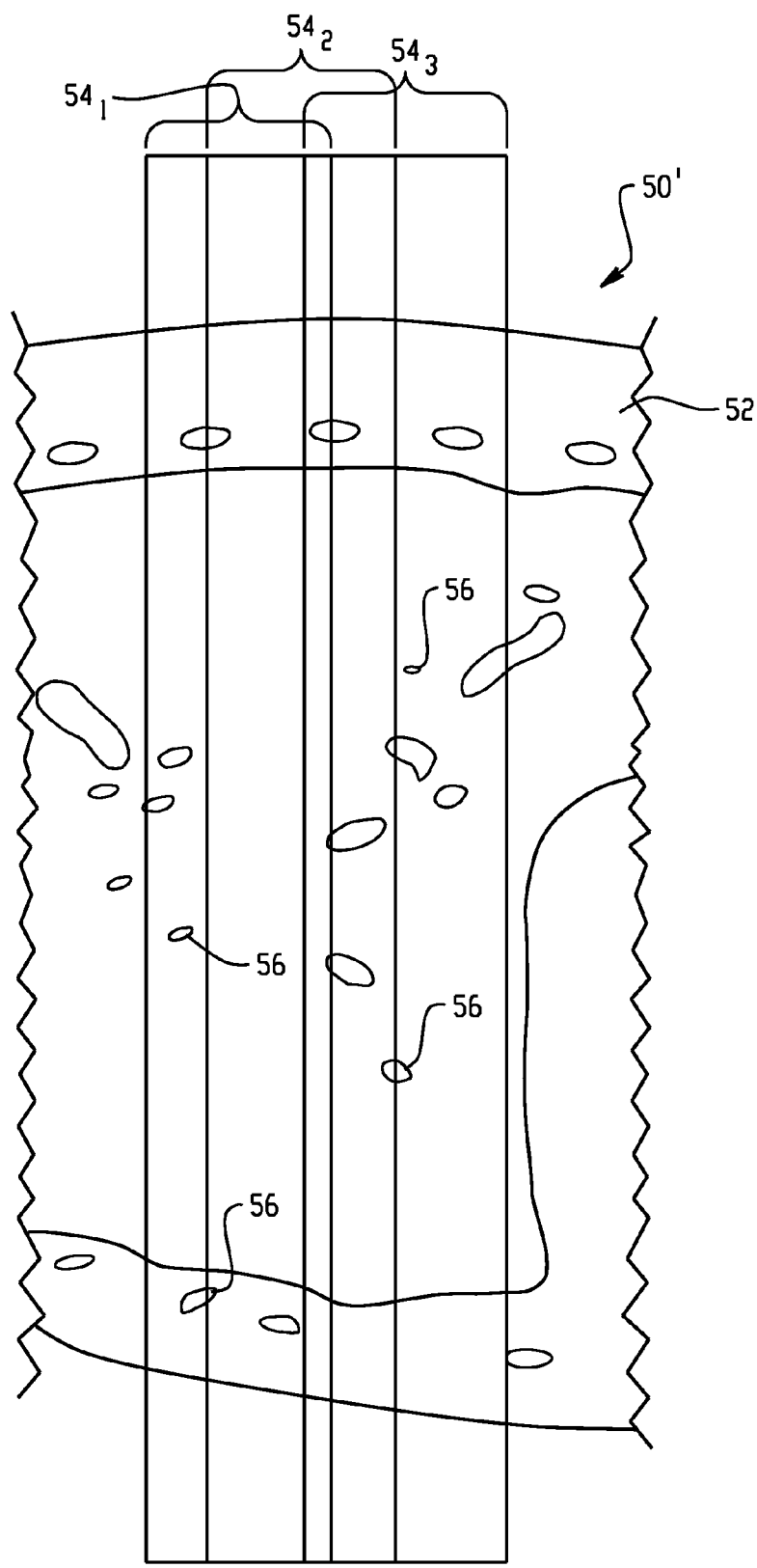
FIG. 2 is a diagrammatic illustration of a section of a coronary artery overlayed with slab sub-volume imaging regions.
Figure 3C:
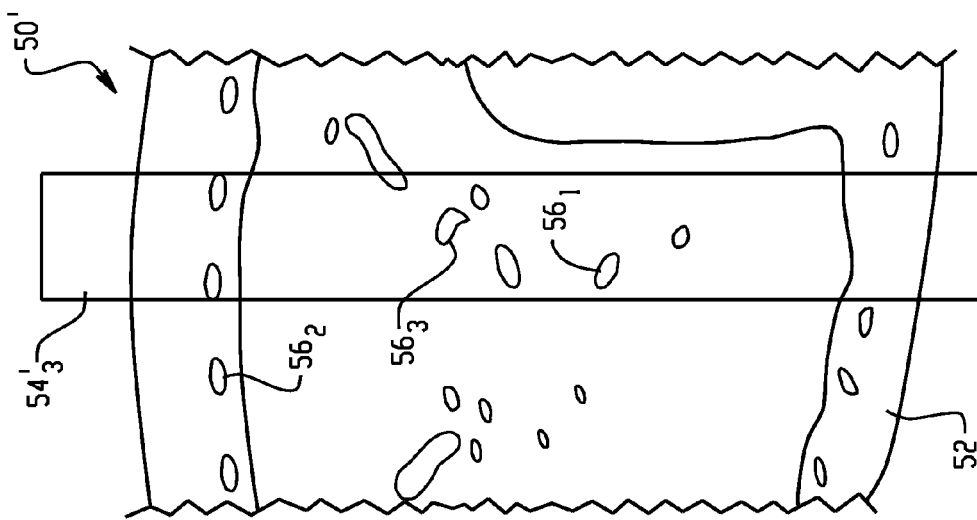
Figure 3B:
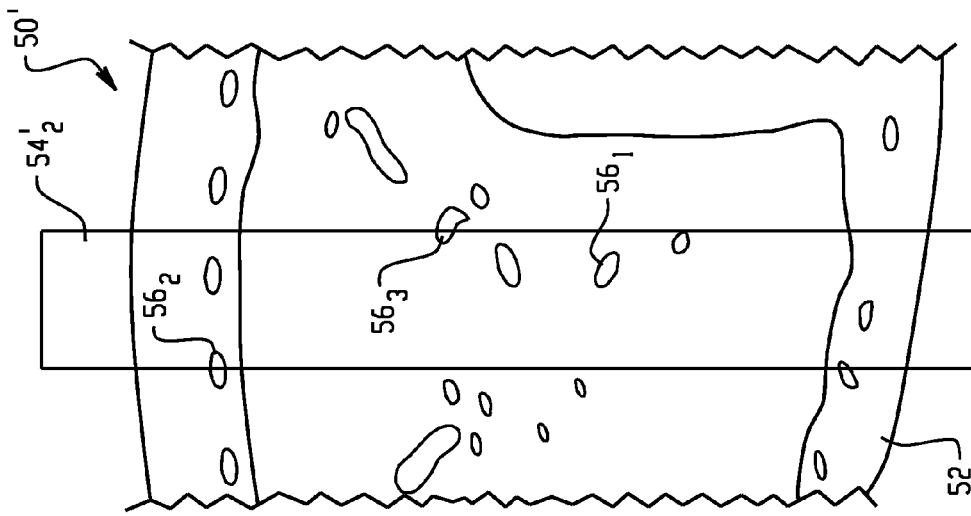
Figure 3A:
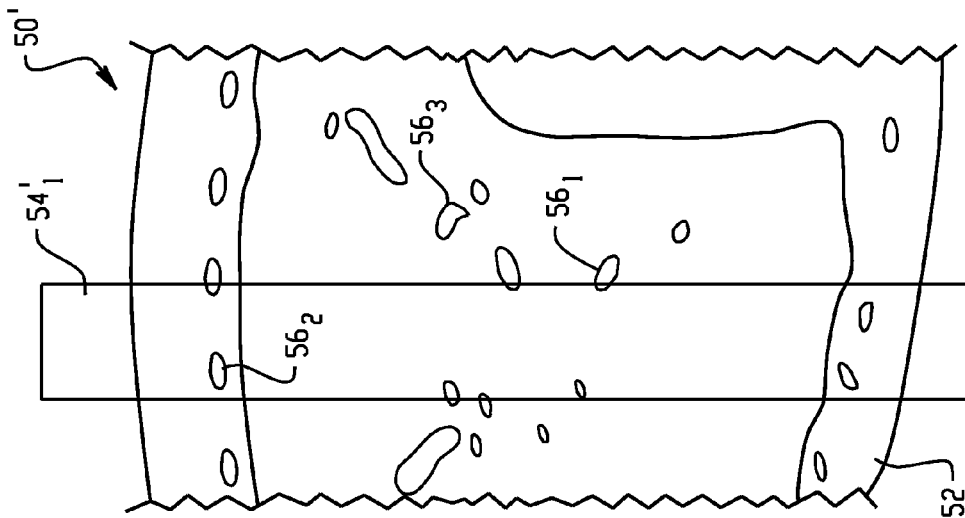

FIGS. 3A, B, and C illustrate three of the sub-volume images of FIG. 2.

A helical CT scanner 10 includes a patient support 12 around which a gantry 14 carrying an x-ray tube 16 and an x-ray detector 18 is rotatably mounted. A means is provided for causing helical motion on the subject support 12 and the x-ray tube 16 and detector 18. In the illustrated embodiment, the means includes a drive 20 moves the patient support 12 longitudinally through the gantry 14. Alternately, the gantry may be moved relative to a stationary patient support. The means further includes a rotary drive 22 for rotating the gantry, with the x-ray tube and detector, around the subject support. Typically, the gantry with the x-ray tube and detector rotates continuously at a relatively high speed, e.g. 200-240 rpm or more. During data acquisition, the relative longitudinal motion between the subject and the x-ray source and detector is selected to have a relatively small relative pitch, e.g. a pitch of 0.2.

The x-ray source 16 projects a cone beam of radiation to the detector 18 which detects a plurality of slices through the image volume concurrently. About every 180 degrees of rotation, a sufficient amount of data from the sub-volume defined by the cone beam is generated to reconstruct a sub-volume image, particularly a slab image with a plurality of transverse slabs. Due to the small pitch the sub-volume images reconstructed from data over the next several revolutions will at least partially overlap the first sub-volume image The generated image data from the detector and axial and rotational position monitors is stored temporarily in a buffer 30. A cardiac gating program or device 32 receives cardiac cycle signals from a cardiac monitor 34, such as an EKG lead system. Data from the sub-volumes in which the cardiac cycle was in a selected phase are stored in a selected cardiac phase data memory 36. If a plurality of cardiac phases are to be imaged, one or more additional cardiac phase data memories 38 may be created or partitioned to save an additional set(s) of data in a different cardiac phase(s).

A sub-volume reconstruction processor 40 reconstructs the data from each of the sub-volumes into a series of sub-volume or slab images which are stored in a corresponding sub-volume or slab image memory 44. A characteristic point routine or processor 46 identifies common characteristic points in each of the sub-volume images. A respiratory motion vector routine or processor 48 calculates respiratory motion 10 vectors which are used by a reconstruction routine or processor 50 when reconstructing the selected cardiac phase data from memory 36 into a volumetric angiographic image, e.g. a volumetric coronary artery image 50'.

With reference to FIG. 2, the angiographic image 50' diagrammatically illustrates a section along the coronary artery 52. A plurality of sub-volumes $54_1, 54_2, 54_3$ are marked along the length of the angiographic image 50'. Because the cardiac gate 32 eliminate sub-volumes which were not collected in the selected cardiac phase, the sub-volumes for which sub-volume images $54'_1, 54'_2, 54'_3$ are generated by the sub-volume reconstruction processor 40 are not uniformly spaced axially along the angiographic image 50' and typically have different degrees of overlap.

When there is no respiratory motion, each of the sub-volume images will be spatially aligned. Each of a plurality of selected characteristic points 56 will typically appear in two or more of the sub-volume images and will overlay each other. However, once the subject starts breathing, the sub-volume images will become displaced from each other and the same characteristic point will be displaced in one of the sub-volume images relative to another.

With reference to FIGS. 3A, 3B, and 3C, three illustrative characteristic points $56_1, 56_2, 56_3$ are shown to each be in an initial position. If sub-volume image $54'_1$ was taken while the subject was still holding its breath (or a selected respiratory cycle reference point), the positions of characteristic points $56_1$ and $56_2$, which can be seen in sub-volume image $54_1$ can be taken as the base or target location. If the patient starts breathing after the data for sub-volume image $54'_1$ is generated and before the data for sub-volume image $54'_2$ is taken, then the locations of the characteristic points $56_1, 56_2,$ and $56_3$ are altered in sub-volume image $54'_2$ relative to their positions in sub-volume image $54'_1$. This motion can be a simple in plane shift or translation along one axes, an in plane translation relative to two axes, translation relative to the axial direction, compression, expansion, or the like. The vector calculating routine or processor 48 calculates a vector which describes the positional movement of the characteristic points in sub-volume image $54'_2$ relative the same character points in the reference sub-volume image $54'_1$. The more characteristic points that are defined, the more precisely the vector can be calculated. Similarly, when the data for the third sub-volume image $54'_3$ is generated, the subject may be in yet another respiratory state or phase which causes the characteristic points to be moved or shifted relative to their positions in sub-volume images $54'_1$ or $54'_2$. The vector calculating processor or routine 48 directly calculates the vector which describes the motion between adjacent and overlapping sub-volume images and indirectly, e.g. through vector addition, calculates the vector which describes the motion between the referenced respiratory phase of each subsequent sub-volume image.

The motion information obtained up to this point of processing is sparse in the time domain. The motion vector for a certain sub-volume corresponds to the middle of the time interval of data used for the reconstruction of it. For a subsequent motion compensated reconstruction using a method like described in D. Schäfer, J. Borgert, V. Rasche, M. Grass, Motion-compensated and gated cone beam filtered back-projection for 3-D rotational X-Ray angiography. IEEE Transactions on Medical Imaging, Vol. 25(7), 898-906, 2006, a temporal interpolation is performed.

Optionally, a respiratory monitor 60 is provided which measures respiration state. This respiration state measurement can be conveyed to the buffer 30 and stored as a part of the sub-volume data. By knowing the respiration state of the collected data, sub-volumes which are collected in like respiration states can be assumed to have a similar respiratory motion correction vector and can be used together to calculate the corresponding respiratory motion vector. The respiratory motion vector can also interpolate the motion vectors determined between each of the sub-volume images into a respiratory motion vector or tensor which describes motion versus time or respiratory phase over all or a relevant portion of the respiratory cycle.

The image reconstruction processor 50 reconstructs the slab or sub-volume data from the slab or sub-volume data 36 in accordance with the determined respiratory motion vectors into the volume image representation 50' for storage in a volume image memory 64. For example, the reconstruction processor evaluates or reconstructs each voxel of the volume image from corresponding voxels or rays of the sub-volume data from memory 36, which corresponding voxels or rays are determined in accordance with the calculated respiratory motion vector corresponding to each sub-volume or the measured respiratory phase.

A video processor 66 under control of a user input device 68 such as a keyboard or mouse, selects the appropriate data from the volume image memory 64 and generates a slice image(s), volume rendering, or other appropriate image for display on a monitor 70.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of CT angiography with respiratory motion compensation comprising:
    rotating a cone beam of radiation around a subject;
    collecting radiation attenuation data from radiation which has passed through a plurality of sub-volumes of the subject;
    longitudinally moving the subject and the cone beam of radiation relative to each other to generate a plurality of sub-volume data sets along a helical trajectory;
    selecting sub-volume data sets from the generated sub-volume data sets which are in a common cardiac phase;
    generating a plurality of sub-volume images in the common cardiac phase from the selected sub-volume data sets;
    identifying characteristic points in overlapping portions of the sub-volume images in the common cardiac phase;
    calculating a respiratory motion vector for at least some of the selected sub-volume data sets in the common cardiac phase based on the identified characteristic points; and
    reconstructing the generated sub-volume data sets into a volume image representation in accordance with the calculated respiratory motion vector.

2. The method according to claim 1, wherein calculating the respiratory motion vector includes:
assessing changes in locations of the identified characteristic points in each of a plurality of the sub-volume images.

3. The method according to claim 1, further including:
monitoring a cardiac cycle of the subject; and
gating the collected sub-volume data sets in accordance with the monitored cardiac cycle.

4. The method according to claim 3, further including:
monitoring a respiratory cycle of the subject; and
using a monitored respiratory phase in calculating the respiratory motion vector.

5. The method according to claim 1, wherein the sub-volume images are slab images with a plurality of transverse slabs reconstructed from a full 180 degree data set.

6. The method according to claim 1, further including:
converting at least a portion of the volume image representation into a human readable display.

7. A non-transitory computer readable storage medium on which a program is stored for controlling a processor to implement the steps according to claim 1.

8. A CT apparatus including one or more processors programmed to perform the method according to claim 1.

9. The CT apparatus according to claim 8, further including:
a subject support;
a rotating gantry;
an x-ray generator mounted on the rotating gantry which generates a cone beam of radiation directed toward the subject support;
a radiation detector which detects the cone beam of radiation after passing through a subject on the subject support; and
a mechanism for causing the cone beam of radiation to rotate around the subject along a helical path.

10. A CT angiography apparatus with respiratory motion compensation comprising:
an x-ray source which generates a cone beam of x-ray radiation rotated around a subject along a helical path;
a detector which generates sub-volume data sets along the helical path corresponding to a plurality of sub-volumes of a blood vessel over a plurality of cardiac cycles;
a cardiac gate which selects sub-volume data sets in a common cardiac phase;
a sub-volume reconstruction routine or processor which generates sub-volume images in the common cardiac phase from the selected sub-volume data sets;
a characteristic point routine or processor which identifies characteristic points in the sub-volume images in the common cardiac phase;
a respiratory motion routine or processor which calculates a respiratory motion vector for at least some of the selected sub-volume data sets in the common cardiac phase based on the identified characteristic points; and
an image reconstruction routine or processor which reconstructs the sub-volume data sets into a volume image representation in accordance with the calculated respiratory motion vector.

11. The apparatus according to claim 10, further including:
a cardiac monitor which monitors a cardiac cycle of the subject; and
a cardiac gate which gates the collected sub-volume image data sets in accordance with the monitored cardiac cycle.

12. The apparatus according to claim 11, further including:
a respiratory monitor which monitors a respiratory cycle of the subject, the respiratory motion routine or processor using the monitored respiratory cycle in calculating the respiratory motion vector.

13. The apparatus according to claim 11, further including:
a monitor which converts at least a portion of the volume image representation into a human readable display.

14. The apparatus according to claim 10, further including:
a memory which stores the sub-volume data sets, the sub-volume reconstruction processor or routine retrieving each set of data from the memory for reconstruction into the sub-volume images and the volume image reconstruction routine or processor retrieving data from the memory for reconstructing the stored data into the volume image representation.

15. The apparatus according to claim 14, further including:
a monitor for converting at least a portion of the volume image representation into a human readable display.

16. A CT angiography apparatus comprising:
a patient support;
an x-ray source and an x-ray detector mounted to a rotatable gantry;
drives configured to move the patient support and the gantry such that to irradiate the patient along a helical trajectory; and
at least one processor connected with the x-ray detector and configured to:
generate sub-volume data sets corresponding to a plurality of sub-volumes of an anatomical region over a plurality of cardiac cycles;
select the sub-volume data sets according to common cardiac phase;
generate sub-volume images from the sub-volume data sets in each common cardiac phase;
identify characteristic points in overlapping portions of the sub-volume images according to each common cardiac phase;
calculate a respiratory motion vector for at least some of the sub-volumes based on characteristic points according to each common cardiac phase; and
reconstruct the sub-volume data sets into a volume image representation in accordance with the calculated respiratory motion vector.

\* \* \* \* \*